United States Patent [19]

Nesbitt

[11] Patent Number: 4,594,999
[45] Date of Patent: Jun. 17, 1986

[54] DISPOSABLE CERVICAL IMMOBILIZATION MEANS

[75] Inventor: William R. Nesbitt, Loomis, Calif.

[73] Assignee: Nesbitt Enterprises

[21] Appl. No.: 650,206

[22] Filed: Sep. 13, 1984

[51] Int. Cl.⁴ .............................................. A61F 5/04
[52] U.S. Cl. .................................. 128/87 R; 128/134
[58] Field of Search ................ 128/87 R, 133, 134, 128/84 C

[56] References Cited

U.S. PATENT DOCUMENTS 4,211,218  7/1980  Kendrick ..................... 128/87 R
4,528,981  7/1985  Behar ............................ 128/133

Primary Examiner—C. Fred Rosenbaum
Assistant Examiner—Karen L. Kaechele
Attorney, Agent, or Firm—Mark C. Jacobs

[57] ABSTRACT

A disposable light weight, easily stored, low cost, cervical spine board made of wax or plastic coated (possibly) segmentally reinforced, double walled, corrugated board or similar radiolucent, flexible, inexpensive, water-resistant material, having score lines therein for folding said board around the sides of the head, and around the sides of the body. Chin tabs are secured and the body fitting wings are secured by duct tape or other two inch tape, optionally pre-attached to said board.

13 Claims, 12 Drawing Figures

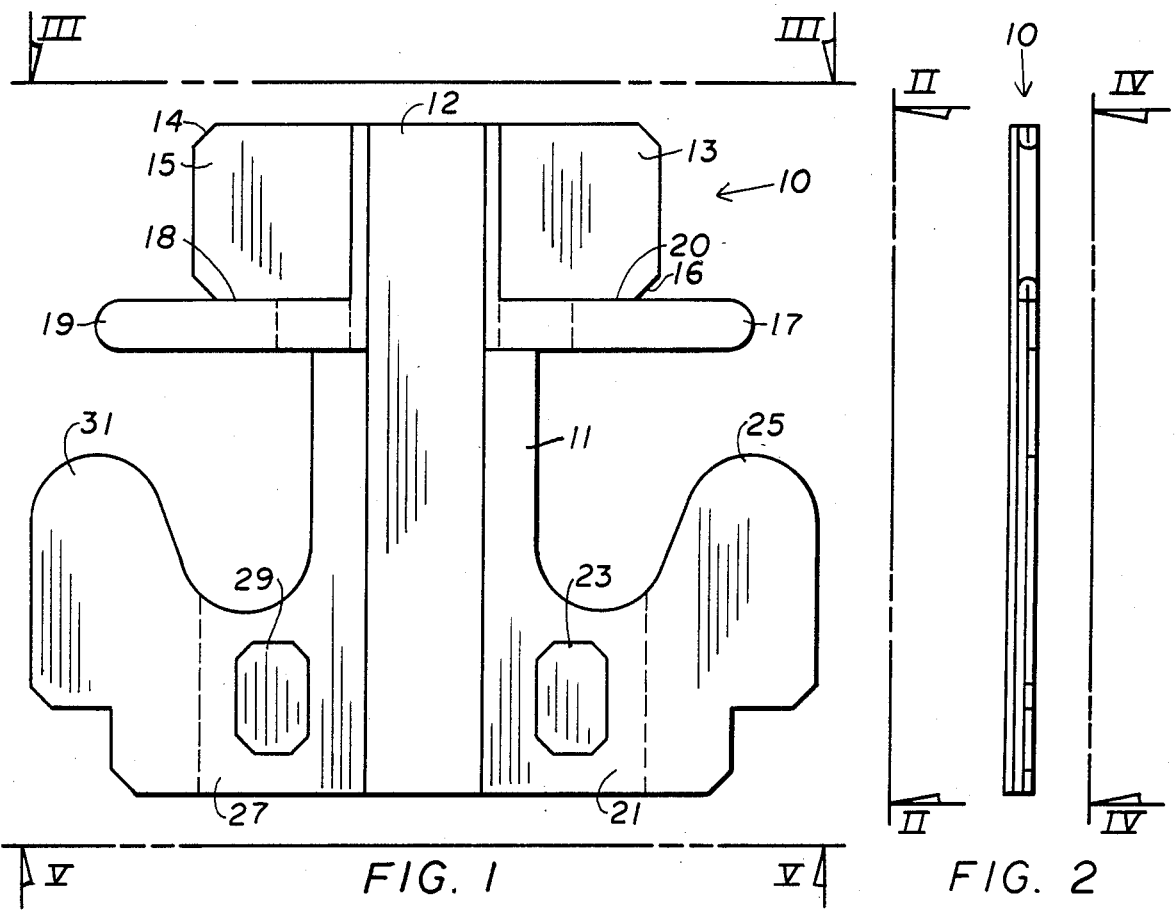
FIG. 1
FIG. 2
FIG. 3
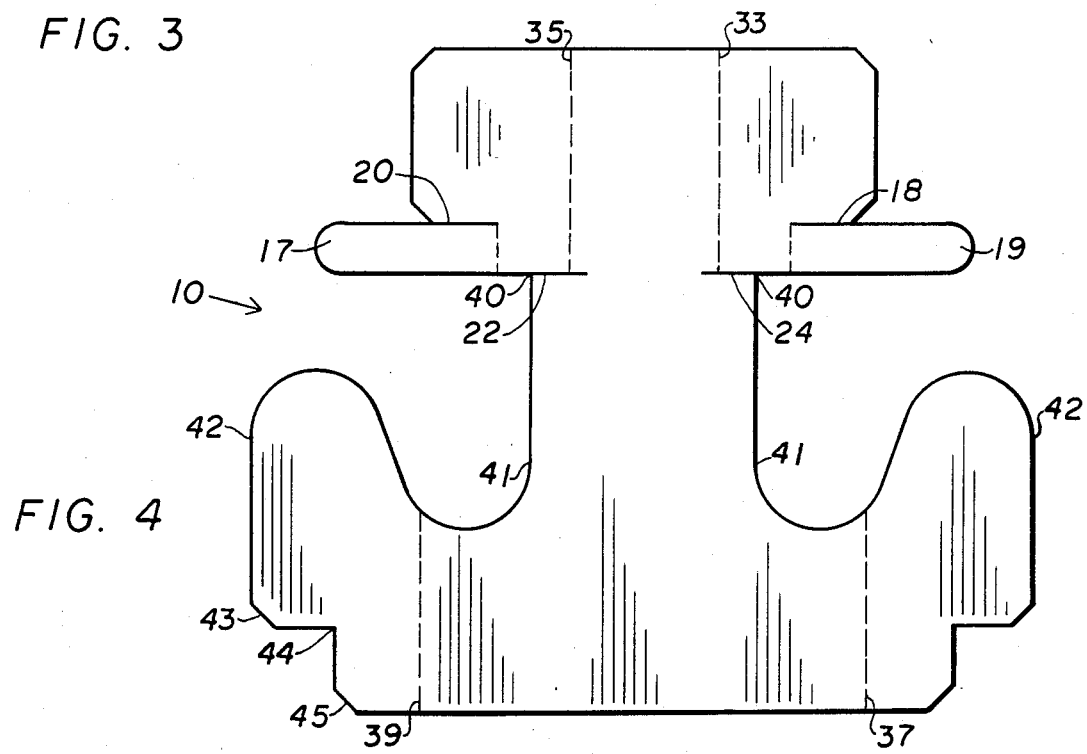
FIG. 4

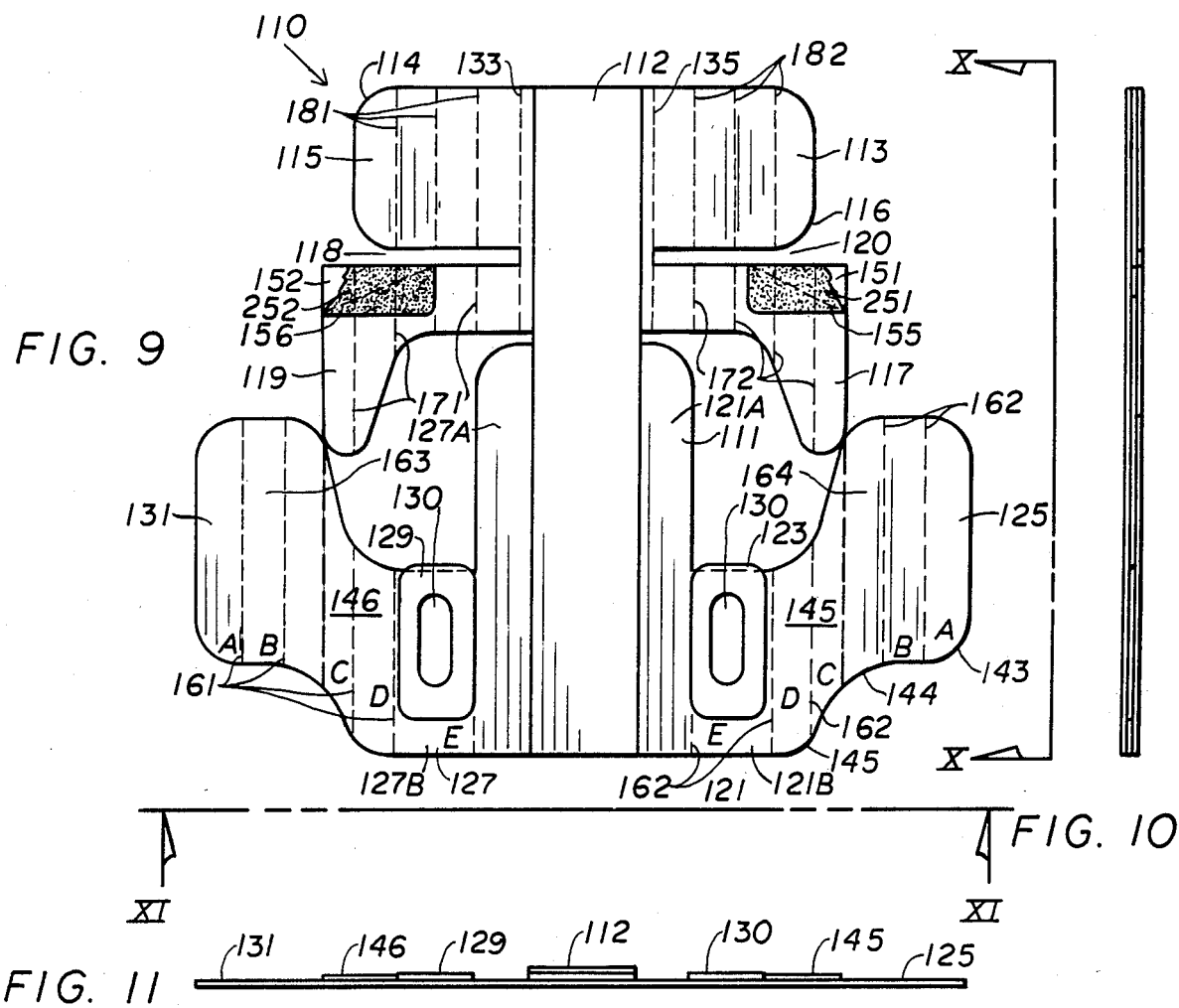
FIG. 9
FIG. 10
FIG. 11
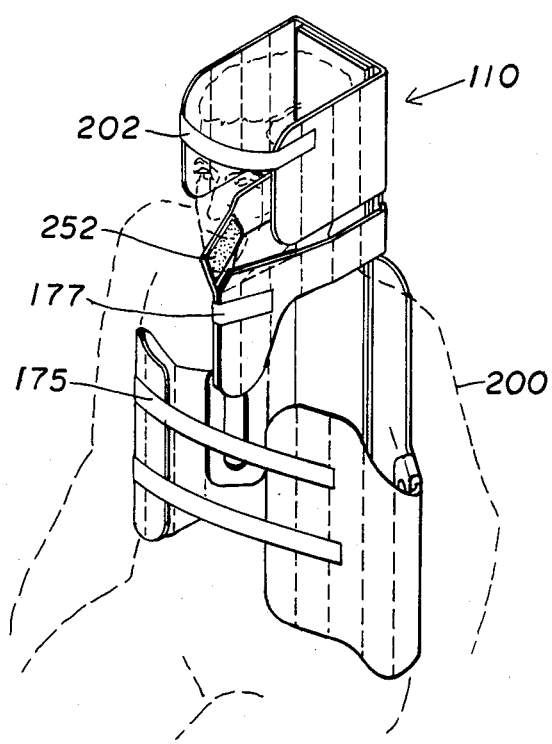
FIG. 12

DISPOSABLE CERVICAL IMMOBILIZATION MEANS

BACKGROUND OF THE INVENTION

1. Field of the Invention

This invention relates in general to devices for immobilizing the human head, neck and torso and relates more particularly to such devices for use in emergency situations to immobilize the body to prevent further injury to the potentially injured cervical spine.

2. Description of the Prior Art

Numerous devices have been proposed in the past to perform the function of immobilizing or stabilizing the human head and neck for emergency purposes. Such devices are extremely important, particularly in emergency situations, in the handling of possible fractures of the cervical spine. In the cases of industrial injuries, automobile accidents and battlefield injuries, it is usually necessary to remove the patient from the injury scene, often under conditions of stress or time pressure, for transportation to medical facilities. This removal is almost always accomplished by personnel who are not medical doctors, although they may have had varying amounts of education and training in the handling of injured patients.

In the handling and moving, there is a high risk of aggravation of injuries to the cervical spine if the patient's head and neck are not properly immobilized or stabilized.

Many prior art U.S. Patents disclose devices comprising a rigid board member having straps attached thereto for attachment to a patient to immobilize the head and neck. They employ strap members which cross the patient's head and are attached to the board to limit movement of the head and neck. These devices provide a rigid structure for completely preventing lateral motion and rotation of the patient's head but are expensive, bulky and complicated to use. Because of their cost, emergency personnel can usually afford to have only one device with them. This not only makes proper immobilization impossible of other injured patients in the same accident but also prevents the emergency personnel from returning to duty until their board is returned. Further the board may not be removed until X-rays have ruled out neck or back injuries. The wood or metal devices presently used allows only very poor quality films when X-rays are shot through them.

There is a need, therefore, for a disposable, inexpensive readily stackable, more radiolucent C-spine immobilizer that can be employed easily by non-physician personnel.

It is another object to provide a cervical spine immobilizer that is easily and quickly applied to injured persons.

Still another object is to provide a spine board that can be stored in large quantities in very little space.

Yet another object is to provide a light weight spine board that is suitable for disaster situations which can be purchased in large quantities at modest expense.

These and other objects of the invention will in part be obvious and will in part appear hereinafter.

The invention accordingly comprises the product possessing the features, properties and the relation of elements which are exemplified in the following detailed disclosure and the scope of the application of which will be indicated in the claims.

For a fuller understanding of the nature and objects of the invention, reference should be had to the following detailed description taken in connection with the accompanying drawings.

DESCRIPTION OF THE FIGURES

FIG. 1 is a front elevational view of the device of this invention's first embodiment.

FIG. 2 is a right side elevational view, the left side being a mirror image thereof.

FIG. 3 is a top plan view.

FIG. 4 is a rear elevational view.

FIG. 9 is a front elevational view of a second embodiment hereof.

FIG. 10 is a view taken along the line X—X of FIG. 9.

FIG. 11 is a top plan view of the second embodiment.

FIG. 12 is a perspective view similar to FIG. 6 showing the use of the second embodiment.

SUMMARY OF THE INVENTION

In accordance with the present invention there is provided a cervical spine immobilization device comprising a double walled, corrugated board member or similar material with additional reinforcing segments. The various portions are held together by standard duct tape or other two inch (2") readily available adhesive tape, or possible pre-attached tapes with removable backing.

The present invention relates to a C-spine restraint especially constructed and arranged for use with emergency patients. Such an occasion might arise in the case of players in an athletic event, multiple car accident, earthquake, battlefield, etc. where plural victims require emergency treatment.

DESCRIPTION OF THE PREFERRED EMBODIMENT

Figure 6:
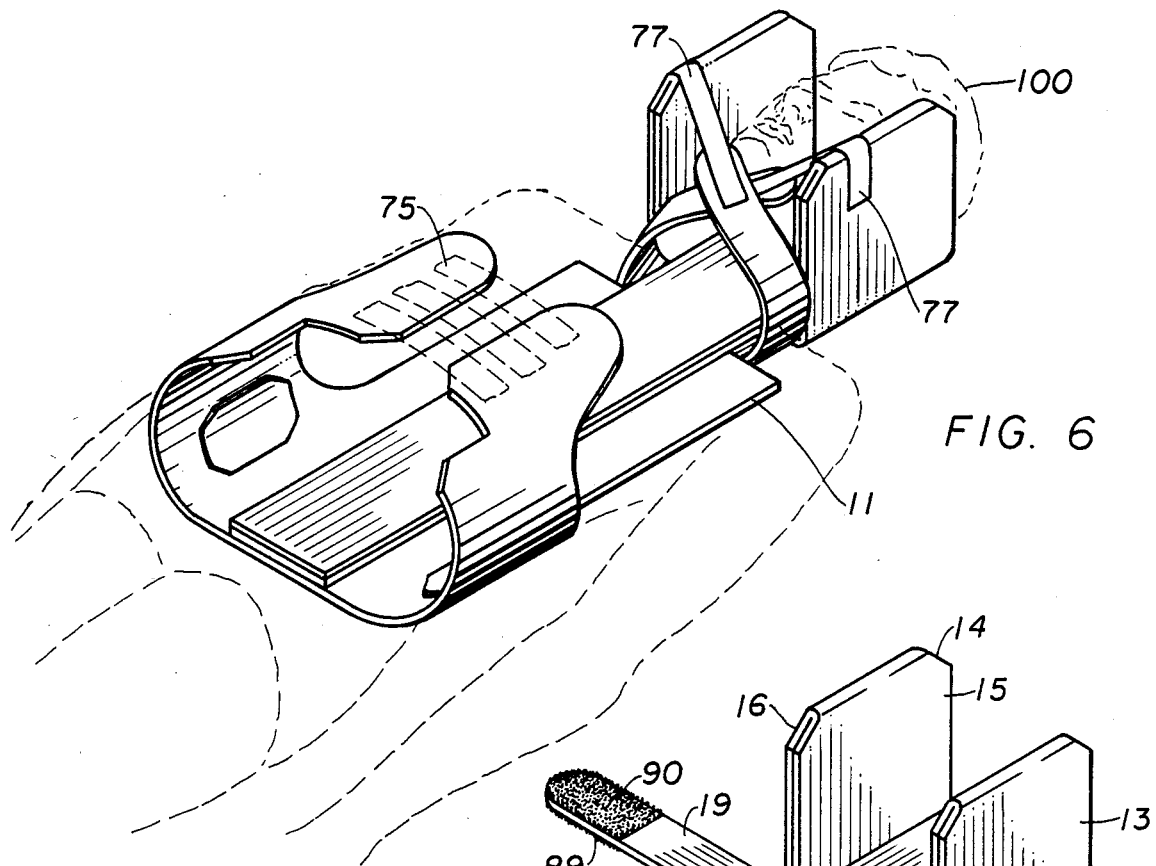
FIG. 6 is a perspective view illustrating the use of the instant device to immobilize a human being. The dotted line indicia on the device forms no part of the design.

The board-like device 10 is formed of double walled, corrugated cardboard or other low cost, throw away, radiolucent material which is preferably treated as by an application of wax or other water resistant film with superposed reinforcing members. It is preferably of a length which will extend from about the top of the head to just above the crotch of a patient. Reference is made to FIG. 6 which illustrates the use thereof.

Figure 5:
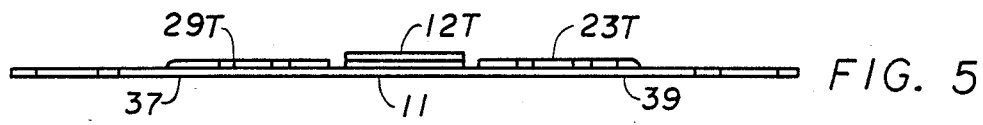
FIG. 5 is a bottom plan view.

As shown in FIG. 5 device 10 includes a main member 11 and superposed members 29T, 12T and 23T all of which will be discussed below.

Device 10 includes a generally longitudinal elongated center portion 12 which comprises preferably three (3) thicknesses of corrugated board or some other inexpensive, rigid material like thin wood or hard plastic. The extra thickness is necessary since the full weight of the patient's back and head are carried by this portion. See FIGS. 5 and 6.

Depending outwardly at the top are head flanges 13 and 15. These are generally rectangular of double thickness with chamfered upper corners 14 and lower corners 16.

Disposed just below said head flanges and also extending outwardly on either side of said center portion 12 are the chin tabs 17 and 19.

Lines 33 and 35 shown in FIG. 4 form the interior edge of both the head flaps and the chin tabs.

Lines 18 and 20 are cut through to isolate the bottom edge of the respective head flanges from its adjacent chin tab. The extension inward shown as 18A and 20A in FIG. 4 makes it easier to arcuately bend and twist the chin tabs 17 and 19 toward each other during useage as illustrated in FIG. 6 so that the tabs lie flat under and along the edge of the patient's jaw to slightly extend the neck. The preferred mode is to employ the imaginary lines to thereby prevent the chin tabs from coming too close to the neck of the injured party, and also this possible destruction of the tab is prevented by not having them capable of flapping around loosely since they are secured in part to the head flaps.

Cut lines 22 and 24 extend through the cardstock and separate the chin tabs from the body portions 21 and 27.

The board is attached to the patient's body by head and neck straps so that the patient may be easily transported with the device in place.

Preferably the chin tabs have an arcuate distal edge as shown in the drawing. This is to prevent possible cuts of the operator's hands on sharp corners and to prevent the victim from being injured by sharp corners should the chin tab come in contact with the neck of the injured party.

As is seen the chin tabs are about 30 to 45% wider horizontally than the head flaps. This is because the head flaps only are folded upwardly from the flat plane parallel to the ground, while the chin tabs are folded over further and twisted upward such that they can lie against the under side of the mandible (jaw), while not impinging on the throat of the victim.

The body portions 21 and 27 disposed on opposite sides of the center each include a double thick inner support members 23 and 29, respectively, or similar inexpensive, thin, rigid, segments of support and a single thickness wing member 25 and 31 respectively. Reference is made to FIGS. 3 and 5 which illustrate the thickness of each of these sections. Note that the full length centre 12 is triple thick when made from double-walled corrugated cardboard. The score lines 37 and 39 illustrated in FIG. 4 constitute the line of demarcation between triple and double thickness corrugated board.

In FIG. 5 the "T" reference is used to help denote the extra thickness not discernible in either FIGS. 1 or 4. Score lines 37 and 39 visible in FIGS. 1 and 4 indicate the lines for folding and storing, both on the chin tabs and torso section.

In the preferred mode, the wings include a cut corner to avoid the thighs when applied to a patient in a sitting position such as in an automobile.

Let us turn briefly to the configuration of the preferred embodiment of the body portions 21 and 27, only one of which will be described since they are mirror images.

Body portion 21 which since the view is reversed in FIG. 4 appears on the left side of the page, commences at a point 40, a few inches distant from the centre 12 along the bottom edge of the chin tabs 17 and 19. The outer edge of the body portion 21 depends vertically to a point 41 and then outwardly in a sinusoidal curve which includes first a valley and then a peak of substantially equal size, since curve ending at a point 42 and which curve forms the top edge thereof; then vertically downward parallel to the centre axis to a preferably chamfered corner 43 and which the edge traverses inwardly and horizontally to a point 44 and then downward about an equal amount as inward to a point 45, which point 45 also preferably constitutes a chamfered corner to a point of termination 47 which is on a line contiguous with the bottom edge of the centre 12.

FIG. 2 not previously discussed is merely a side view of the device 10 which helps illustrate the fact that the device can be readily flat packed in large pluralities for major catastrophes. There are no straps or buckles to add thickness.

FIG. 6 illustrates the use of the device 10. The board 11 is laid on the ground with centre portion 12 facing toward the back of the victim 100. Head flaps 13 and 15 are folded upwardly thereby bringing the chin tabs up as well. These latter are then folded inwardly toward each other and twisted as above and secured as in FIG. 6 with tape 77 and across forehead tape 101. The wings 25 and 31 are folded upwardly and inwardly around the sides of the body to a spaced relationship of about 2 to 3 inches apart wherein the undersides thereof are then secured to each other by strips of duct tape 75. This immobilizes both the head and the thorax. Note how the top edge of the inner supports 23 and 29 lie firmly flat thereby helping to support the victim.

The sinusoidal curves are seen to permit the arms to extend downwardly in a natural position next to the body but exterior to the device 10.

Figure 7:
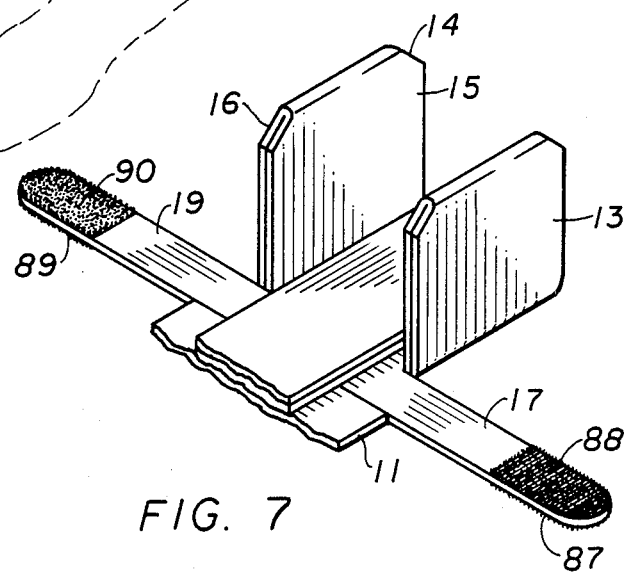
FIG. 7 is a closeup perspective view similar to FIG. 6 or a variant of a portion of this invention.

In FIG. 7 we see a slight variant to the instant device. Here Velcro ® strips made by Velcro S.A. of Fribourg Switzerland are used as the closure means. In this embodiment, the tabs are designated 87 and 90 and the respective strips of the securing means are designated 88 and 89. While not shown, it is obvious to the skilled artisan that Velcro can also be used to secure the chest portions as well. Velcro, however, adds to the device's expense.

The device is of such a size that it can be placed on a patient in a confined area without first requiring removal of the patient from the confined area. Because of its size and configuration, several can be easily stowed in an ambulance so as to be out of the way, such as under the ambulance gurney mattress, while still being readily available for use.

The device has the advantage that it may be readily and effectively used by personnel who are not medical doctors, since it requires no attachment to the human body. Hence, the device may remain on the patient during transportation to the hospital, in the emergency room, and in the radiology area until X-rays have been taken to determine the presence of cervical spine fractures. This eliminates the need for handling of patients with their neck and head in an unstabilized condition, and thus prevents the possibility of catastrophic injury to the cervical spine during movement of the patient.

In addition because the device is made of flexible, disposable material it is infinitely maleable such that it can be bent to accommodate different size and shapes of bodies. Even a whole child can be laid into the device if necessary.

In FIG. 3 an optional but preferable wax or other water repellant coating 46 is shown on the outer surface of the device. Also water proof glue would be used to retain structural integrity. This mode of manufacture is a must to enable the device to be used by ski patrols or in wet weather or wet locations.

Figure 8:
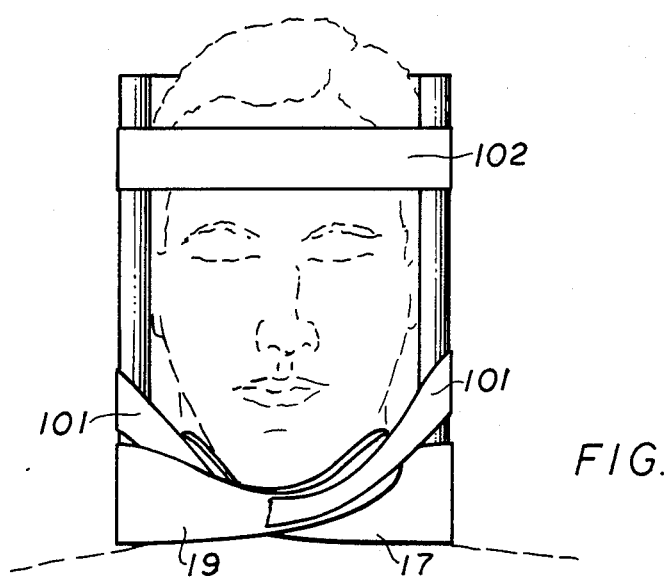
FIG. 8 is a closeup view of a portion of FIG. 6.

Optionally there may be included preferably reinforced hand grip slots 61 which are reinforced as per FIG. 1 by circumsrcibed fabric or plastic film overlays. These grip holes or slots can be used to more easily move patients to and from gurneys when the appliance is applied to them, as well as for grasping a plurality of the instant devices for transportation. While shown in the first view only the reinforcement can be applied on the rear per FIG. 4. FIG. 8 is a closeup of the application of device 10 to the head area. Note how the chin tabs 17 and 19 are twisted to lie flat, and tape is applied cross wise for maximum patient comfort. Tape member 101, which would ordinarily be used, was omitted from FIG. 6 for ease of viewing.

While shown in the figures as having chamfered corners such as 14, the device 10 may be supplied with rounded corners as well. The purpose is merely to avoid contact of a sharp pointed corner with the hand of the operator or the facial area of the injured party. Such rounded corners are shown in the second embodiment in FIG. 9.

As shown in FIG. 10, the second embodiment and designations, device 110 includes a main member 111 and several superposed members all of which will be discussed below.

Device 110 includes a generally longitudinal elongated center portion 112 which also comprises preferably three (3) thicknesses of corrugated board or some other inexpensive, rigid material. Depending outwardly at the top are head flanges 113 and 115. These are generally rectangular of double thickness with preferably rounded upper corners 114 and lower corners 116.

Disposed just below said head flanges and also extending outwardly on either side of said center portion 112 are the neck collar 117 and 119. Score lines 133 and 135 form the interior edge of both the head flaps and the hard neck collar member 117 and 119.

Slots 118 and 120, usually about ½" in elevation, are cut through to isolate the bottom edge of the respective head flanges from its adjacent collar members.

The hard collar members 117 and 119 comprise generally outwardly extending, mirror image, 90° inwardly inverted, boot-like portions secured to central member 11. These include vertical score lines 171 and 172. Portions 117 and 119 include a built in chin tab 151 and 152 within the upper distal corner relative to the central member 112. These chin tabs are preferably padded on the underside as with a urethane foam layer 251 and 252, which is visible in FIG. 12. Diagonal score lines 155 and 156 are used to fold back the top section of the chin tabs 151 and 152 to conform to the bone structure of the patient. Note the angularity as in FIG. 12 of the chin tab. The boot-like portions 117 and 119 also have rounded edges at the lower end thereof, again to avoid injury to the patient.

The board 110 is attached to the patient's body at head and neck so that the patient may be easily transported with the device in place in like manner as embodiment 1.

The single thickness body portions 121 and 127 disposed on opposite sides of the center each include double thick, inner support segment 129 and which has a slot therethrough 130 to serve as a hand grip. The body portions are also constructed of similar inexpensive, thin, rigid material. Reference is made to FIGS. 9 and 11 which illustrates the thickness of each of these sections. Note that the full length center 112 is triple thick relative to the other aspects of the embodiment. It is also seen that segments 129 are not disposed within the total top to bottom distance of the body segments 129. See FIG. 9. These L-shaped, outwardly extending, mirror image segments are disposed adjacent the central section 112, and extend outwardly to vertical score line 161D. The outward extending areas 127B and 121B commence at score line 161E which is a continuation of the main segment of the body portion 127A and 121A.

The wing members 125 and 131 begin coextensive with the top and bottom edges of the outward extending area of the body portions 127 and 121.

The wing members 131 and 125 commence along score lines 161D and 162D on the proximal side adjacent the body support 129 and 130 and comprise a first portion 146 and 145 that extend generally outwardly and upwardly at the bottom and generally upwardly and outwardly at the top in a divergent relationship to connect to a rounded corner generally rectangular portion 163 and 164. The upper and the lower outer corners of which are convex and the lower inward corner of which is concave.

FIG. 12 illustrates the use of embodiment 110 wherein the head areas 113 and 115 are joined by tape 202 in a manner similar to that shown at 102 in FIG. 8. Heavy adhesive tape, duct tape or any tape at hand may be employed.

The hard collar sections are closed by the application of tape 177 and the body sections by two tapes 175.

Whereas the chin tabs 17 and 19 are crossed over each other per FIG. 8 and secured by tapes 101, there is no need to do in the instant embodiment in a separate manner since the hard collar serves to immobilize the neck area and is secured together by the tape 177. However, upon application of the hard collar and the closure thereof, the score lines 155 and 156 should be folded outwardly to relieve pressure on the chin of the patient.

It is seen that the instant embodiment incorporates all of the benefits of the first embodiment plus the extra benefit of a hard cervical collar such that in those instances where a collar is called for, separate appliance need not be used for that purpose.

The corrugated board used in both embodiments of this invention should preferably be dipped, sprayed, or otherwise coated with a waterproofing agent such as a wax or plastic coating. This procedure will insure wet weather durability.

Since certain changes may be made in the above apparatus and without departing from the scope of the invention herein involved it is intended that all matter contained in the above description is illustrative and not in a limiting sense.

I claim:

1. A disposable light weight radiolucent cervical spine board adapted to restrain the head and body of an injured person comprising
    a flat, elongated, central member of a rectangular configuration, extending the length of the board,
    a pair of head flaps, one of which extends outwardly on either side of said central member and which flaps are capable of moving from a first position in the same plane as said central member to a second position generally normally upward from said central member,
    a pair of chin tabs, one on each side of the central member also extending outwardly from said central member and extending further than said head flaps, movable from the same first position through same second position to a third position inwardly toward each other, and adapted to serve as a hard collar for neck immobilization, a pair of body portions, one on each side of said central member, said body portions including a flat support member adjacent to said central member, and a wing member capable of moving from a first position in the same axis as the central member upwardly and inwardly toward the other of said wing members to a spaced relationship second position opposed to the other of said wing members, and wherein a score line separates the head flaps and chin tabs from the central section.

2. In the device of claim 1 wherein a score line separates each support section from its respective wing member.

3. In the device of claim 1 wherein each wing member has a right angle notched corner.

4. In the device of claim 1 wherein the chin tabs have an arcuate outer edge.

5. In the device of claim 1 wherein the central section is reinforced and the head support sections double thick relative to the thickness of the balance of said device.

6. In the device of claim 5 wherein the device is constituted of double walled, corrugated board.

7. In the device of claim 1 wherein each chin tab includes a Velcro ® closure portion on the underside thereof.

8. In the device of claim 1 wherein the wing members also include Velcro ® closures on the underside thereof.

9. In the device of claim 1 wherein each of the body portions comprising the support member have a sinusoidal curve top edge spaced down from the chin tabs.

10. In the device of claim 9 wherein the body portions have a notched lower, outer corner.

11. In the device of claim 10 wherein the head flaps are rounded at their corners and the chin tabs are arcuate at their outer edge.

12. In the device of claim 11 wherein the chin tabs extend outward from said central section more than said head flaps but less than said body portions.

13. In the device of claim 1 wherein the device is slot free.

* * * * *